United States Patent [19]

Stubbs et al.

[11] 4,171,355

[45] Oct. 16, 1979

[54] CERTAIN TICKICIDAL PYRETHROID MIXTURES AND STABILIZER THEREFOR

[75] Inventors: Vincent K. Stubbs, Caboolture, Australia; Francis S. Downing, Macclesfield; Gordon J. Marrs, Windsor, both of England

[73] Assignee: ICI Australia Limited, Melbourne, Australia

[21] Appl. No.: 839,201

[22] Filed: Oct. 4, 1977

[30] Foreign Application Priority Data

Oct. 5, 1976 [AU] Australia .............................. 7614/76

[51] Int. Cl.$^2$ .............................................. A01N 9/02
[52] U.S. Cl. .................... 424/174; 424/200; 424/304; 424/305; 424/331
[58] Field of Search .................. 424/174, 200, 331

[56] References Cited

U.S. PATENT DOCUMENTS

| | | | |
|---|---|---|---|
| 3,287,453 | 11/1966 | McHattie | 424/200 |
| 3,996,244 | 12/1976 | Fujimoto et al. | 424/275 |

FOREIGN PATENT DOCUMENTS 2615646  4/1976  Fed. Rep. of Germany.

*Primary Examiner*—V. D. Turner
*Attorney, Agent, or Firm*—Cushman, Darby & Cushman

[57] ABSTRACT

A process for killing ticks using a composition comprising a pyrethroid of the cyclopropane carboxylate type, a hetero N-substituted phosphorus compound and a hydroxy-substituted benzophenone.

5 Claims, No Drawings

CERTAIN TICKICIDAL PYRETHROID MIXTURES AND STABILIZER THEREFOR

This invention relates to the stabilization of pyrethroids and to tickicidal compositions containing such stabilized pyrethroids and which are useful in animal husbandry.

The pesticidal properties of naturally occurring pyrethroids, such as pyrethrum from pulverized flowers, have been known for many years and such properties are attributed to esters of chrysanthemic acid present in the flowers and which are often referred to as pyrethrins, cinerins and jasmolin. However these chrysanthemates have the serious drawback of being decomposed easily by the action of light or heat. Synthetic derivatives of the pyrethrins, such as allethrin and its isomers, were made in about 1949, but these materials also suffered from the deficiency of being decomposed to some extent by light. More recently in Australian Patent Specification No. 484 834 there has been described a class of cyclopropane carboxylic acids and esters which has pesticidal properties. Whilst these synthetic pyrethroidal compounds are more stable than the naturally occurring pyrethroids they are nevertheless prone to decomposition when acted upon by heat and light especially ultra-violet light.

It has been proposed in Australian Patent Specification No. 475 461 to stabilize insecticidal compositions comprising a chrysanthemate against decomposition by heat or light by the use of alkaline earth metal oxides or tertiary amines. Such a process suffers from the disadvantage that it is difficult to disperse inorganic materials in chrysanthemates in a matter such that uniformity and homogeneity of the dispersion may be maintained over prolonged periods. Whilst the use of tertiary amines is more satisfactory it is essential when such stabilizing agents are used that they be of very high purity—and thus of high cost—to ensure that there is an absence of basic impurities which are known to decompose chrysanthemates. It has also been proposed in German Offenlegungsschrift No. 2,615,646 to stabilize a synergized microencapsulated composition which is stated to be useful as an insecticide and comprising as an active ingredient pyrethrins and pyrethroids which are stabilized with 4-dodecyloxy-2-hydroxybenzophenone and which are synergized by piperonyl butoxide.

In the realms of animal husbandry it is known that whereas certain pesticidal compositions are useful as insecticides, they are rarely useful on an economic basis for combatting ixodial infestations such as infestations of ticks on sheep, dogs or cattle. Even when some strains of ticks are susceptible initially to treatment by conventional insecticides it has been found that such "susceptible" strains become less affected by such treatment with the passage of time and in due course a proportion of these ticks are converted to a strain which is resistant to such treatment.

In Australia, as well as in other countries, a problem of considerable economic importance is the control of ticks (*Boophilus mircoplus*) which infest cattle. In the past "susceptible" or "non-resistant" strains of ticks have been controlled by means of sprays or dips using as active ingredients certain chemicals such as carbamates, chlorinated hydrocarbons or organophosphates. However more recently it has been found that certain strains of cattle ticks have emerged and are now wide spread in Australia and elsewhere and are spreading further and which are not affected by certain of the broad spectrum pesticides normally used for this purpose. These strains are known as "resistant" strains of cattle ticks and represent a most serious problem of the Australian cattle industry.

A typical "susceptible" strains is the "Yeerongpilly" strain which is widely distributed and is controlled readily with commerical pesticides such as 1-naphthyl N-methylcarbamate, dichlorodiphenyltrichloroethane (DDT) or a wide range of organophosphorus pesticides including compositions containing as an active ingredient chemicals commonly named bromophos-ethyl, chloropyrifos, coumaphos, dioxathion, ethion or pirimiphos-ethyl. It is used by all authorities in Australia as the "susceptible" reference standard against which the degree of resistant strains is measured.

A typical resistant strain is the "Biarra" strain also known as the "Esk" or "Anderson" strain, and it has become increasingly resistant to organophosphorus tickicides with the passage of time since it was isolated in the Esk district of Queensland, Australia in 1966. Other strains of cattle tick which are resistant to organophosphorus tickicides include the so called "Mount Alford" strain and the "Mackay" strain. Certain strains of cattle tick may become resistant to treatment with tickicides after prolonged treatment therewith. For example whilst DDT was effective as a tickicide when it was first used for the purpose, there are now strains of tick which are immune to treatment with DDT at concentrations which are economic. It is highly desirable that new tickicides be developed so that the cattle tick has little or no resistance to the tickicides when it is first used. Such tickicides should be effective in controlling and killing cattle ticks of both the "susceptible" strains and the strains which are resistant to tickicides already in use. Unless a tickicide is active against both the "resistant" and "susceptible" strains, the long range effect of treatment in a given treatment area is not to control cattle ticks, but merely to increase the population of the "resistant" strain in relation to that of the "susceptible" strain.

In our copending Australian patent applications 26309/77 and 28193/77 which documents are incorporated herein by reference we have described pesticidal compositions which comprise mixtures of pyrethroids and organophosphorus compounds which are synergistically active as ixodicides, for example they are very useful in controlling infestations of ticks of the *Boophilus spp.* It has now been discovered that the period during which synergistic compositions comprising mixtures of pyrethroids and organophosphorus compounds are effective as tickicides may be prolonged in tropical and sub-tropical latitudes if there is incorporated into such a composition a stabilizingly effective amount of a non-basic organic stabilizing agent capable of absorbing ultra-violet light. The use of such more persistent compositions has facilitated the control of ixodial infestations such as infestations of cattle ticks (*Boophilus microplus*) of susceptible strains such as the "Yeerongpilly" strain and of strains which are resistant to common tickicides such as certain organophosphorus compounds, certain carbamates or DDT and which include strains commonly referred to in Australia as "Biarra", "Mount Alford", "Mackay", "Esk" or "Anderson" strains.

Accordingly in one embodiment of the invention there is provided a new composition of matter comprising as a tickicidally effective active ingredient a mixture comprising as a first component at least one pyrethroid, as a second component at least one organophosphorus compound and as a third component at least one non-basic organic stabilizing agent said agent being characterized in that it absorbs light having a wavelength in the range from 300 to 400 millimicrons.

From amongst suitable stabilizing agents mention is made of certain groups of compounds known to absorb ultra violet light and including benzophenones, benzotriazoles, benzylidene malonates, salicylates, substituted acrylonitriles, triazines, benzoates and nickel organo compounds.

From amongst the group of benzophenones a particularly useful sub group is the class of hydroxy-substituted benzophenones, which also may be optionally alkoxy-substituted, for example those disclosed in British Pat. No. 892,264. From amongst the group of benzotriazoles it has been found that hydroxyphenyl benzotriazoles such as the 2(3', 5'-dialkyl-2'-hydroxyphenyl) benzotriazoles are very useful. Typical examples of suitable stabilizing agents include
2-hydroxy-4-n-octoxybenzophenone,
2-hydroxy-4-dodecyloxybenzophenone,
2,2'-dihydroxy-4-methoxybenzophenone,
2,2'-dihydroxy-4,4'-dimethoxybenzophenone,
2,4-dihydroxybenzophenone,
2,2',4,4'-tetrahydroxybenzophenone,
2-(2'-hydroxy-5'-methylphenyl)benzotriazole,
2-(2'-hydroxy-3',5'-di-t-amylphenyl)benzotriazole,
2-(2'-hydroxy-3',5'-di-t-butylphenyl)benzotriazole,
2-(2'-hydroxy-3',5'-di-t-butylphenyl)-5-chlorobenzotriazole,
p-methoxybenzylidene malonic acid dimethyl ester,
p-octylphenyl salicylate,
2-ethylhexyl-2-cyano-3,3-diphenyl acrylate,
1,3,5-tris(2'-hydroxyphenyl)triazine,
Resorcinol monobenzoate,
Nickel bis(octylphenyl)sulphide, and
[2,2'-thiobis-(4-t-octylphenolato)]-n-butylamine nickel.

Pyrethroids which may be stabilized by our process include naturally occurring materials such as pyrethrum esters typically the well known pyrethrins 1 and 2, the cinerins 1 and 2, and jasmolin 2. Synthetic pyrethrins such as allethrin (dl-2-allyl-3-methylcyclopent-2-en-4-ol-1-onyl dl cis-transchrysanthemate) and isomers thereof, and other esters of chrysanthematic acid such as barthrin(6-chloropiperonyl chrysanthemumate) and its bromo analogue, cyclethrin(3-(2 cyclopentenyl)-2-methyl-4-oxo-2-cyclopentenyl chrysanthemumate) or dimethrin(2,4-dimethylbenzyl chrysanthemumate) may also be stabilized by our process. Our process is particularly advantageous for the stabilization of the cyclopropane carboxylic acids and esters described in the specification of Australian Patent 484 843 which document is incorporated herein by reference. As typical examples of such cyclopropane carboxylic acids and esters mention is made of
5-benzylfur-3-yl methyl (±)-cis, trans chrysanthemate,
5-benzylfur-3-yl methyl(±)-trans chrysanthemate,
5-benzylfur-3-yl methyl(±)-cis chrysanthemate,
3-phenoxybenzyl(±)-cis,trans -3-(2,2-dichlorovinyl)-2,2-dimethylcyclopropane carboxylate,
3-phenoxybenzyl(±)trans-3-(2,2-dichlorovinyl)-2,2-dimethylcyclopropane carboxylate,
α-cyano-3-phenoxybenzyl(±)cis, trans-(2,2-dichlorovinyl)-2,2-dimethylcyclopropane carboxylate,
α-cyano-3-phenoxybenzyl(±)cis, trans-(2,2-dibromovinyl)-2,2-dimethylcyclopropane carboxylate, and
3-phenoxybenzyl(±)-cis-3-(2,2-dibromovinyl)-2,2-dimethylcyclopropane carboxylate.

The nature of the organophosphorus compound may be varied widely. For example suitable organophosphorus compounds include aliphatic compounds, aromatic compounds or compounds comprising heterocyclic rings. Typical classes of organophosphorus compounds suitable for use in the invention include organophosphates (which may be represented typically by the chemical known by the common name of chlorofenvinphos); phosphorus bearing phenyl esters (typically bromophos-ethyl), which optionally may contain sulphur bearing substituents (typically fenthion); phosphorus bearing derivatives of thioethers (typically ethion); or phosphorylated heterocyclic ring compounds having at least one oxygen or nitrogen atom in the heterocyclic ring (typically coumaphos, or diazinon). Particularly useful organophosphorus compounds include those wherein the phosphorus bearing radical is a phosphate, a phosphorothioate, a phosphorodithioate, or a di(phosphorodithioate). Examples of typical organophosphorus compounds suitable for use in the invention are tabulated below in Table 1. In referring to these compounds they are described as set out in the well known and authorative dictionary of pesticides and chemical pollutants entitled "Nanogen Index", published by Nanogens International, of Freedom, USA, 1975 edition and having a Library of Congress Catalog Card Number 75-14751. For ease of description and identification the compounds are also referred to by their common name and by a designation (indicated by an inverted word in inverted commas) which is a registered trade mark in some countries. A particularly preferred organophosphorus compound for use in the invention is 0,0-diethyl 0-(2-diethyl-amino-6-methyl-pyrimidin-4yl) phosphorothioate, commonly referred to as pirimiphosethyl, and this may advantageously be combined with a (±) cis, trans isomer mixture of 3-phenoxybenzyl 2,2-dimethyl-3-(2,2-dichlorovinyl) cyclopropane carboxylate, which is often referred to as NRDC 143, and a stabilizing agent such as 2-hydroxy-4-n-octoxybenzophenone in a composition or process according to the invention.

TABLE 1

| Chemical Name | Common Name | Invented Word |
|---|---|---|
| Mixed cis/trans isomers of 2-chloro-1-(2,4-dichlorophenyl)vinyl diethyl phosphate | chlorfenvinphos | "Birlane" |
| 0-(4-bromo-2,5-dichlorophenyl) 0,0-diethyl phosphorothioate | bromophos-ethyl | "Nexagan" |
| 0,0-diethyl 0-3,5,6-trichloro-2-pyridyl-phosphorothioate | chloropyrifos | "Dursban" |
| 0,0-diethyl 0-(3-chloro-4-methyl-7- | coumaphos | "Asuntol" |

TABLE 1-continued

| Chemical Name | Common Name | Invented Word |
| --- | --- | --- |
| coumarinyl) phosphorothioate | | |
| O,O-diethyl O-(2-isopropyl-6-methyl-4-pyrimidinyl) phosphorothioate | diazinon | "Basudin" |
| O,O-dimethyl O-p-(dimethylsulphamoyl) phenyl phosphorothioate | famphur | "Famophos" |
| O,O-dimethyl O-(3-methyl-4-methylthiophenyl) phosphorothioate | fenthion | "Baycid" |
| O,O-diethyl O-(2-diethylamino-6-methyl-pyrimidin-4-yl) phosphorothioate | pirimiphos-ethyl | "Primicid" "Solgard" |
| S-[(p-chlorophenylthio)-methyl] O,O-diethyl phosphorodithioate | carbo-phenothion | "Trithion" |
| S,S'-p-dioxan-2,3-diyl O,O,O',O'-tetraethylphosphorodithioate | dioxathion | "Delnav" |
| O,O-dimethyl phthalimido methyl phosphorodithioate | phosmet | "Prolate" |
| O,O,O',O'-tetraethyl-S,S'-methylene di(phosphorodithioate) | ethion | "Nialate" |

The compositions of the invention may be in the form of concentrates containing for example from about 5 to 50% of the pyrethroidal component, and such concentrates may be diluted with tickicidally inert material prior to use so that the tickicidally effective ingredient constitutes from 0.0025 to about 5% w/w and often from 0.01 to 0.1%, of the diluted composition. The inert material may be solid or liquid, and the latter, particularly aqueous liquid formulations, are preferred. Emulsifiable solutions or suspensions of the active material may be prepared by dissolving or suspending it in a solvent, or a mixture of solvents, which is non-toxic to the infested animals onto which the composition is to be applied, adding an emulsifier and/or wetting agent and, optionally, adding some water. A typical emulsifiable concentrate formulation of this type for use in our process could comprise 30% by weight of active ingredient, 45% by weight of mineral oil, 10% by weight of a mixture of nonionic and anionic emulsifiers and 15% by weight of a substantially aromatic high boiling solvent.

Our compositions may also be dispersible powders wherein the active ingredient is mixed together with an inert solid carrier such as powdered chalk, talcs, clays, kieselguhr, bentonite and a dispersing agent. Suitable emulsifying and dispersing agents are known from the prior art; anionic, cationic and nonionic agents may be used. A suitable nonionic emulsifier is for example the condensation product of nonylphenol with ethylene oxide available commercially under the Registered Trade Mark "Lissapol" N; suitable dispersing agents are for example the disodium salt of dinaphthylamethane disulphonate, sodium lauryl sulphate and the condensation product of alkylphenol with ethylene oxide available commercially under the Registered Trade Mark "Lubrol" E. Our compositions may also be concentrated aqueous pastes, dusts, oily solutions or aerosols.

Suitable dose rates of the active ingredient for the control of infestations of cattle tick on cattle are not narrowly critical and are dependent to some extent on the strain of tick being treated. Rates will also be related to the mode of application of the active ingredient, for example the rate will vary for each type of application such as dipping, spraying or dusting of the infested surface. As a general guide dips containing up to 1% w/w of active ingredient are satisfactory for most degrees of severity of infestation by "resistant" strains of tick and adequate ixiodic control may be effected in many instances where the concentration of active ingredient in a dip is in a range from 0.005 to 3% w/w. When the composition is a dispersion of powder in an aqueous medium, concentrations of the active ingredient may sometimes need to be somewhat higher, say up to about 5% w/w.

The ratio of the components of the pesticidally active material in our compositions may be varied to suit the conditions under which the composition is to be used and also to provide an economic, effective composition dependent on the cost of the components and the extent to which the composition exhibits synergism. By synergism we mean the cooperative action of two or more agents in a composition in such a way that the total effect is greater than the sum of the individual effects taken individually. Suitable compositions include those having a weight ratio of the first component to the second component in a range from 5:1 to 1:5. At the present time the cost of certain of the pyrethroidal components, such as those of the the permethrin type, is more than the cost of an equal weight of the organophosphorus component and thus from an economic aspect it is desirable when permethrin type components are used that the organophosphorus component comprise at least half of the pesticidal mixture in the compositions of the invention. Preferably therefore in such compositions the weight ratio of the first component to the second component lies in a range from 1:1 to 1:5, and often in a range from 1:1 to 1:2.

The amount of stabilizer, or combination of stabilizers, used in the compositions of the invention, will vary dependent to some extent on the degree of stability required of the compositions, on the inherent instability of the unstabilized pyrethroid or on the conditions under which the compositions are to be used. Thus in instances wherein a composition is used within a building such as a byre or in an area in which the intensity of light is small then it is convenient to use a composition wherein the weight ratio of the pyrethroidal component to the stabilizing component is about 100:1. On the other hand it is convenient to use compositions wherein such a ratio is about 2:1 when the composition is used under conditions which promote relatively rapid destabilization of the pyrethroidal component. Such conditions are encountered out of doors in sub-tropical and tropical latitudes in which the ambient temperatures and the proportion of ultra violet light in the sunlight are comparatively high. It is under such conditions that synergized compositions according to the invention and comprising pyrethroids are used to control ixodidal infestations on animals and wherein prolonged activity of the pyrethroid is highly desirable especially for example wherein cattle are infested with cattle tick (*Boophilus microplus*). For some purpose adequate tickicidal compositions are obtained when the above ratio of the pyrethroidal component to the stabilizing component is intermediate of the above values, for example in a range from 50:1 to 4:1 and more usually from 20:1 to 6:1. The stabilizing component can be mixed with the pyrethroidal component or incorporated into the tickicidal composition by means of conventional blending techniques.

In a further embodiment of the invention there is provided a process for stabilizing a tickicidal composition comprising at least one pyrethroidal component and at least one organophosphorus compound which process comprises adding to and mixing with said compositions a stabilizingly effective amount of a stabilizing agent comprising at least one non-basic organic compound capable of absorbing light having a wavelength in a range from 300 to 400 millimicrons.

In a still further embodiment of the invention there is provided a process for killing ticks, especially ticks of the Boophilus spp., and particularly cattle ticks (*Boophilus microplus*), which process comprises treating media infested with ticks with a tickicidally effective amount of a mixture comprising as a first component at least one pyrethroid, as a second component at least one organophosphorus compound and as a third component at least one non-basic organic stabilizing agent, said agent being characterized in that it absorbs light having a wavelength in a range from 300 to 400 millimicrons.

The compositions of the invention may be used to provide more prolonged tickicidal activity against ixodidal infestations, especially against infestations of cattle tick of both the "susceptible" strains and the "resistant" strains in any of the adult, larval or the intermediate stages, than has hitherto been possible at similar concentrations of unstabilized mixtures of pyrethroids and organophosphates. The resultant prolonged protection given to animals against such infestations by the embodiments of the invention is of considerable economic since it enables the frequency of tickicidal treatment of animals to be reduced, thereby reducing the cost of maintaining the animals in a healthy condition.

Our invention is now illustrated by, but is not limited to, the following examples in which all parts and percentages are on a weight basis unless otherwise specified.

EXAMPLE 1

A first composition was prepared by mixing 25 parts of 3-phenoxybenzyl($\pm$)-cis,trans-3-(2,2-dichlorovinyl)-2,2-dimethylcyclopropane carboxylate, 125 parts of pirimiphosethyl, 45 parts of mineral oil available commercially under the designation of "Shell" 21, 6 parts of a composition comprising a blend of anionic surfactants and available commerically under the designation "Atlox" 3404F, 3 parts of a nonionic surfactant available commercially under the designation "Teric" 17A6 and 99 parts of an aromatic solvent available commercially under the designation "Aromasol" H. ("Shell", "Atlox", "Teric" and "Aromasol" are registered trade names). A portion of this composition was diluted with water to provide a dilute composition containing 250 parts of the carboxylate component per million parts of the dilute composition (ppm), and to this dilute composition there was added an amount of a toluene solution of "Teric" 17A6 and 2-hydroxy-4-n-octoxybenzophenone to provide 100 ppm of 2-hydroxy-4-n-octoxybenzophenone in a first emulsion which was according to the invention. For the purpose of comparison there were prepared in a similar manner a second emulsion which was not according to the invention and which contained 250 ppm of the above carboxylate and 1250 ppm of the above organophosphorus compound. There was also prepared a third emulsion which was not according to the invention and which contained 250 ppm of the above benzophenone derivative.

Into each of the three emulsions prepared as above there was dipped a group of 30 test tubes in a manner such that the exterior surface of each tube was wetted with the emulsion. The group of tubes was divided into three subgroups each of 10 tubes; a first sub-group was stored in the dark, a second sub-group was exposed to sub-tropical sunlight for 60 hours and a third sub-group was exposed similarly for 80 hours. 10 larval cattle ticks of the "Biarra" strain were placed on the surface of each of the stored and exposed tubes and the average time taken for the ticks to be dislodged from the surface was recorded. The results obtained are set out in Table 2 and it is apparent that the residue from the first emulsion according to the invention is more effective in killing larval ticks than is the comparative second emulsion. The residue from the comparative third emulsion was lacking in tickicidal activity under the experimental conditions used and the results therefrom are not tabulated.

TABLE 2

| Composition | 1st emulsion | Comparative 2nd emulsion. |
|---|---|---|
| Exposure time of treated surface (hours) | Time for ticks to be dislodged from the treated surface (minutes). | |
| 0 | 6.6 | 6.5 |
| 60 | 11.8 | 17.9 |
| 80 | 23.4 | 44.5 |

EXAMPLE 2

A concentrated emulsifiable composition was prepared by mixing 20 parts of alphacyano-3-phenoxybenzyl($\pm$) cis,trans-(2,2-dichlorovinyl)-2,2-dimethylcyclopropane carboxylate, 40 parts of 0,0-diethyl 0-(3-chloro-4-methyl-7-coumarinylphosphorothioate, 10 parts of 2-(2'-hydroxy-5-methylphenyl) benztriazole, 5 parts of "Teric" 200 and 5 parts of "Kemmat" SC15B and adding to the mixture sufficient toluene to produce a composition of 100 parts by volume. ("Teric" 200 is a registered trade name for a nonionic surfactant obtained by condensing nonylphenol with ethylene oxide and propylene oxide. "Kemmat" SC15B is a registered trade name for an anionic surfactant comprising a 70% solution of calcium dodecylbenzene sulphonate in a nonaqueous solvent). The composition so prepared was emulsified with sufficient water to provide a first sprayable emulsion which contained 125 parts of the carboxylate component per million parts of the emulsion. The first emulsion so obtained was sprayed on two year old calves weighing approximately 150 kilograms at the rate of 5 liters per calf. The calves were heavily infested with all stages of the susceptible "Yeerongpilly" strain of cattle tick. For the purpose of comparison a second sprayable emulsion was prepared and used in a manner similar to that above except that the benztriazole derivative used in the first emulsion was omitted. This comparative emulsion was only 80% as effective in providing protection against the ticks as was the emulsion according to the invention when the calves were allowed to graze in pastures in the sub-tropical latitutes of Australia.

EXAMPLE 3

A dispersible powder was prepared by mixing 100 parts of alpha-cyano-3-phenoxy benzyl(±)cis,trans-(2,2-dibromovinyl)-2,2 dimethylcyclopropane carboxylate, 300 parts of 2-chloro-1-(2,4-dichlorophenyl)vinyl diethyl phosphate, 1 part of 1,3,5-tris(2'-hydroxyphenyl)triazine, 500 parts of clay, 20 parts of a nonionic surfactant available commercially under the designation of "Teric" N8 and 80 parts of water. This composition when dispersed in water to give a concentration of 1% of the carboxylate component was effective in giving prolonged protection against cattle tick to housed cattle on to which the composition was sprayed.

EXAMPLE 4

A first composition was prepared by mixing 100 parts of 3-phenoxybenzyl(±)-cis,trans-3-(2,2-dichlorovinyl)-2,2-dimethylcyclopropane carboxylate, 200 parts of 0,0,0'0'-tetraethyl-S,S'-methylene di(phosphorodithioate), 25 parts of p-octylphenyl salicylate, 405 parts of mineral oil "Shell" 21, 54 parts of "Atlox" 3404F, 27 parts of "Teric" 17A6 and 189 parts of "Aromasol" H. A portion of this composition was diluted with water to provide a dilute composition containing 125 ppm of the carboxylate component. For the purposes of comparison there was prepared in a similar manner a second composition which was not according to the invention and which differed from the first composition in that it did not contain any p-octylphenyl salicylate component. 5 calves which were infested with adult cattle ticks of the "Mount Alford" strain were sprayed with the above first composition at a rate of 1 liter of composition per 30 kilograms of body weight and were then allowed to graze in the open in Southern Queensland. Similarly 5 calves were treated with the second composition. It was found that the first composition provided on average about 10% more protection, expressed in days before a retreatment spray was necessary, than the protection provided by the second comparative composition.

EXAMPLE 5

An emulsifiable composition was prepared by mixing 10 parts of alpha-cyano-3-phenoxybenzyl(±)cis,trans-2,2-dichlorovinyl)-2,2-dimethylcyclopropane carboxylate, 20 parts of S,S'-p-dioxan-2,3-diyl 0,0,0', 0'-tetraethylphosphorodi-thioate, 1 part of nickel bis(octylphenyl)sulphide, 5 parts of "Teric" 200, 5 parts of "Kemmat" SC15B and sufficient toluene to produce a composition of 124 parts by volume. The composition so prepared was emulsified with sufficient water to provide an emulsion containing 0.03% w/v of the carboxylate component. When sprayed at a rate of 1 liter per 30 kilograms of body weight on to grazing cattle infested with cattle tick of the "Biarra" strain the emulsion so prepared was effective in combatting the infestation and prevented reinfestation of the cattle more effectively than did a comparative emulsion which did not contain any nickel bis(octylphenyl)sulphide.

EXAMPLE 6

A composition was prepared by mixing 100 parts of 3-phenoxybenzyl(±)-cis,trans-3-(2,2-dichlorovinyl)-2,2-dimethylcyclopropane carboxylate, 200 parts of 0,0-diethyl 0-(2-isopropyl-6-methyl-4-pyrimidinyl)phosphorothioate, 0.5 part of 2-ethylhexyl-2-cyano-3,3-diphenyl acrylate, 1.5 parts of 2,2'-dihydroxy-4,4'-dimethoxybenzophenone, 405 parts of mineral oil "Shell" 21, 54 parts of "Atlox" 3404F, 27 parts of "Teric" 17A6 and 189 parts of "Aromasol" H. The composition so prepared was diluted with water to form a dilute composition containing 250 ppm of the carboxylate component. When this dilute composition was sprayed at a rate of 1 liter per 30 kilograms of body weight on to grazing cattle infested with cattle tick of the "Biarra" strain, it was found to be effective in combatting the infestation and prevented infestation more effectively than did a comparative composition which did not contain either the acrylate or the benzophenone compound.

EXAMPLE 7

The general procedure of Example 6 was repeated except that the amount of the phosphorothioate component was reduced to 100 parts of the 2,2'-dihydroxy-4,4'-dimethoxybenzophenone component was replaced by 4.5 parts of p-methoxybenzylidene malonic acid dimethyl ester. The composition so obtained was an effective, persistent tickicide.

EXAMPLE 8

A composition was prepared by mixing 400 parts of allethrin, 50 parts of 3-phenoxybenzyl(±)-cis,trans-3-(2,2-dichlorovinyl)-2,2-dimethylcyclopropane carboxylate, 50 parts of alpha cyano-3-phenoxybenzyl(±)-cis,-trans-3-(2,2-dichlorovinyl)-2,2-dimethylcyclopropane carboxylate, 50 parts of 0,0-diethyl 0-3,5,6-trichloro-2-pyridylphosphorothioate, 50 parts of 0,0-dimethyl phthalimido methyl phosphorodithioate, 100 parts of 2-hydroxy-4-dodecyloxybenzophenone, 125 parts of 2,4-dihydroxybenzophenone, 400 parts of ethanol 230 parts of mineral oil "Shell" 21, 30 parts of "Atlox" 3404F, 15 parts of "Teric" 17A6 and 500 parts of "Aromasol" H. This composition was diluted with water to provide a dilute composition wherein the pyrethroidal content was 500 ppm. When used as a spray on grazing cattle infested with cattle tick of the "Yeerongpilly" strain it was found to be effective as a persistent tickicide.

We claim:

1. A process for killing Boophilus microplus ticks which process comprises treating media infested with said ticks with a tickicidally effective mixture comprising as a first component, 3-phenoxybenzyl(±)-cis, trans-3-(2,2-dichlorovinyl)-2,2-dimethylcyclopropane carboxylate; as a second component, 0,0-diethyl 0-(2-diethylamino-6-methylpyrimidin-4-yl) phosphorothioate, and as a third component, 2-hydroxy-4-n-octoxybenzophenone, the weight ratio of the said first component to the said second component being in a range from 5:1 to 1:5, and the weight ratio of the said first component to the said third component being in a range from 100:1 to 2:1.

2. A process according to claim 1 wherein the said weight ratio of the said first component to the said second component is in a range from 1:1 to 1:5.

3. A process according to claim 1 wherein the said weight ratio of the said first component to the said second component is in a range from 1:1 to 1:2.

4. A process according to claim 1 wherein the said weight ratio of the said first component to the said third component is in a range from 50:1 to 4:1.

5. A process according to claim 1 wherein the said weight ratio of the said first component to the said third component is in a range from 20:1 to 6:1.

* * * * *